{ | United States Patent [19] | [11] Patent Number: | 5,895,756 |
|---|---|---|
| Barrett et al. | [45] Date of Patent: | Apr. 20, 1999 |

[54] NON-ANTIBIOTIC SYSTEM FOR SELECTION OF RECOMBINANT MYCOBACTERIA

[75] Inventors: Alan D. T. Barrett, Galveston; David Niesel, League City; Christopher Robb, Galveston; Haolin Ni, Galveston, all of Tex.

[73] Assignee: The Board of Trustees of the University of Texas System, Austin, Tex.

[21] Appl. No.: 08/840,101

[22] Filed: Apr. 11, 1997

[51] Int. Cl.$^6$ .................. C12P 21/04; A61K 39/003; C12N 15/00; C12N 1/12

[52] U.S. Cl. .................. 435/69.7; 424/184.1; 424/199.1; 424/204.1; 435/172.3; 435/253.1; 935/14; 935/29; 935/41; 935/45

[58] Field of Search .................. 424/199.1, 184.1, 424/204.1; 435/68, 69.7, 172.3, 253, 317, 320, 320.1; 935/14, 29, 41, 45

[56] References Cited

U.S. PATENT DOCUMENTS 4,769,327   9/1988   Stephens et al. .................. 435/68
5,514,375   5/1996   Paoletti et al. .................. 424/199.1

OTHER PUBLICATIONS

Jacobs et al, "Mycobacteriophage vector systems", Reviews of Infectious Diseases, vol. 11, supplement 2, pp. s404–s410, Mar. 1, 1989.

Dellagostin et al "Construction and use of integrative vectors to express foreign genes in mycobacteria", Molecular Microbiology, vol. 10, No. 5, pp. 983–993, Sep. 1, 1993.

Kremer et al, "analysis of the Mycobacterium tuberculosis 85 A antigen promoter region", Journal of Bacteriology, vol. 177, No. 3, pp. 642–653, Feb. 1, 1995.

*Primary Examiner*—James C. Housel
*Assistant Examiner*—Rodney P. Swartz
*Attorney, Agent, or Firm*—Benjamin Aaron Adler

[57] ABSTRACT

The present invention provides a *Mycobacterium-E. coli* shuttle vector containing sequences coding for a tribrid fusion containing the *M. leprae* 18kDa antigen sequence, a phoA protein antigen sequence and a non-mycobacterial, non-*E.coli* heterologous protein antigen sequence. Also provided is a method of producing protective immunity in an animal or human host in need of such treatment, comprising the step of administering to said animal or human host an effective dose of recombinant mycobacteria carrying the vector of the present invention.

6 Claims, 10 Drawing Sheets

NON-ANTIBIOTIC SYSTEM FOR SELECTION OF RECOMBINANT MYCOBACTERIA

BACKGROUND OF THE INVENTION

1. Field of the Invention

The present invention relates generally to the fields of molecular biology and vaccinology. More specifically, the present invention relates to a non-antibiotic system for selection of recombinant mycobacterium.

2. Description of the Related Art

*Mycobacterium bovis* bacille Calmette-Guerin (BCG) is the most extensively utilized attenuated live vaccine in the world today. Recent advances in mycobacterium vectors hold great promise for the development of effective and inexpensive recombinant-based vaccines. However, the use of antibiotic resistance genes for the selection of recombinant mycobacterium in preparation of the vectors remains problematic. It is inadvisable to administer a vaccine containing an antibiotic resistance gene if it can be avoided.

Dengue is caused by four serologically related viruses known as dengue types 1, 2, 3 and 4, which are found in most tropical parts of the world (including the Caribbean and Mexico) infecting approximately 20 million annually with a mortality rate of 5%. Dengue is an emerging disease that is spreading through the Americas and is likely to be increasingly introduced into Texas from Mexico. There are no vaccines currently available to prevent dengue.

The prior art is deficient in the lack of an effective non-antibiotic system for selection of recombinant mycobacteria such as *Mycobaterium bovis* BCG, *mycobacterium smegmatis* or other mycobacteria that may have potential as vaccines. The present invention fulfills this longstanding need and desire in the art.

SUMMARY OF THE INVENTION

In one embodiment of the present invention, there is provided a composition of matter comprising a Mycobacterium shuttle vector containing sequences coding for a heterologous antigen sequence, e.g., dengue virus envelope (E) protein as a fusion containing the *M. leprae* 18Kda antigen and a *E. coli* phoA protein antigen sequence.

In another embodiment of the present invention, there is provided a method of producing protective immunity in an animal or human host in need of such treatment, comprising the step of administering to said individual an effective dose of an immunogen, i.e., a mycobacterium host carrying and expressing the vector of the present invention such as.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows an overview of the strategy used to construct tribrid fusion protein with 18 kDa, phoA and heterologous protein antigen sequences.

FIG. 2 shows the origin and manipulation of the *E. coli* phoA sequence.

FIG. 3 shows the vector, pUS909 which contains the *Mycobacterium leprae* 18 kDa antigen sequence, and sequences enabling the vector to multiply in *E. coli* and an insertion sequence which allows stable maintenance in mycobacterium. Molecular biological manipulation of the phoA sequence into pUS909 results in the vector, pCR7.

FIG. 4 shows an example of the contstruction of a tribrid fusion vector where Dengue 4 envelope protein gene o sequences has been inserted into pCR7 at the restriction enzyme site, BglII, At the junction between the 18 kDa and the phoA sequences.

FIG. 5 shows a Western blot of the fusion product in *E. coli. E. coli* strains were grown in LB for 16 hours. Whole cell lysates were prepared for SDS PAGE. Immunodetection was carried out using anti-AP primary polyclonal antibody, followed by goat anti-mouse AP conjugated antibody. Lane A is *E. coli.* with pUS909; Lane B is *E. coli.* with pAT43-17 (a positive control); Lane C is an *E. coli.* transformant with a negative diagnostic restriction digest; Lane D is *E. coli.* with pCR7, a transformant with a positive restriction digest.

FIG. 6 shows that *M. smegmatis* transformed with pCR7 expresses a 61 kDa "PhoA" fusion protein. Bacterial strains were grown at 30° C. for 16 hours. Whole cell lysates were prepared for SDS PAGE. Immunodetection was carried out using pre-absorbed anti-AP primary polyclonal antibody, followed by goat anti-rabbit HRPO conjugated antibody. Lane 1: *E. coli* with pAT43-17 (a positive control); lane 2: *M. smegmatis;* lane 3: *M. smegmatis* with pUS909; lane 4: *M. smegmatis* with pCR7-7, a transformant which turned blue over 2 weeks; lane 5: *M. smegmatis* with pCR7-12, a transformant which turned blue over 4 weeks.

FIG. 7 shows *M. smegmatis* transformed with pCR7 which expresses a 61 kDa "18kDa" fusion protein. *M. smegmatis* strains were grown in NB no. 2 for 48 hours. Whole cell lysates were prepared for SDS PAGE. Immunodetection was carried out using L5 primary monoclonal antibody, followed by goat anti-mouse AP conjugated antibody. Lane A: *M. smegmatis* ; lane B: *M. smegmatis* pUS909; lane C: *M. smegmatis* pCR7-7; and lane D: *M. smegmatis* pCR7-12.

FIG. 8 shows that each *M. smegmatis* pCR7 transformant had one insertional event. *M. smegmatis* chromosomal DNA was extracted and digested with BamHI. Samples were separated on a 0.8% agaraose gel and transferred to NCM. NCM was probed with a PCR amplified, radiolabeled phoA fragment. Lanes: (A) *M. smegmatis;* (B) *M. smegmatis* with pUS909; (C) *M. smegmatis* with pCR7-7; and (D) *M. smegmatis* with pCR7-12.

FIG. 9 shows that the 18 kDa::phoA fusion protein is upregulated in a macrophage cell line. Immunoblot of whole extracts of J774 and *M. smegmatis*. J774 cells were infected or not with pCR7-7*M. smegmatis* (moi 50:1) for 24 hours. *M. smegmatis* were isolated from J774 monolayers by solubilization and centrifugation. Extracts were obtained by sonication and boiling in SDS-sample buffer. Equivalent amounts of protein were loaded for pCR7-7 and pCR7-7/J774. A monoclonal antibody to PhoA was used as a primary antibody, followed by a HRPO conjugated GAM. Detection was by ECL.

FIG. 10 shows that *M. smegmatis* transformed with pCR7 is PhoA+. *M. smegmatis* was transformed with either pCR7 or pUS909 and plated on NB no. 2 agar plates with 50 micrograms/ml X-P chromophore. After colonies appeared (3 days) plates were stored in the dark at 4 degrees C for 4 weeks. All the pCR7 transformed bacteria turned blue during this time. Transformant pCR7-7 turned blue over 2 weeks. Shown here: isolation streak of pCR7-7 and pUS909 transformed *M. smegmatis*.

DETAILED DESCRIPTION OF THE INVENTION

Definitions

Figure 1:
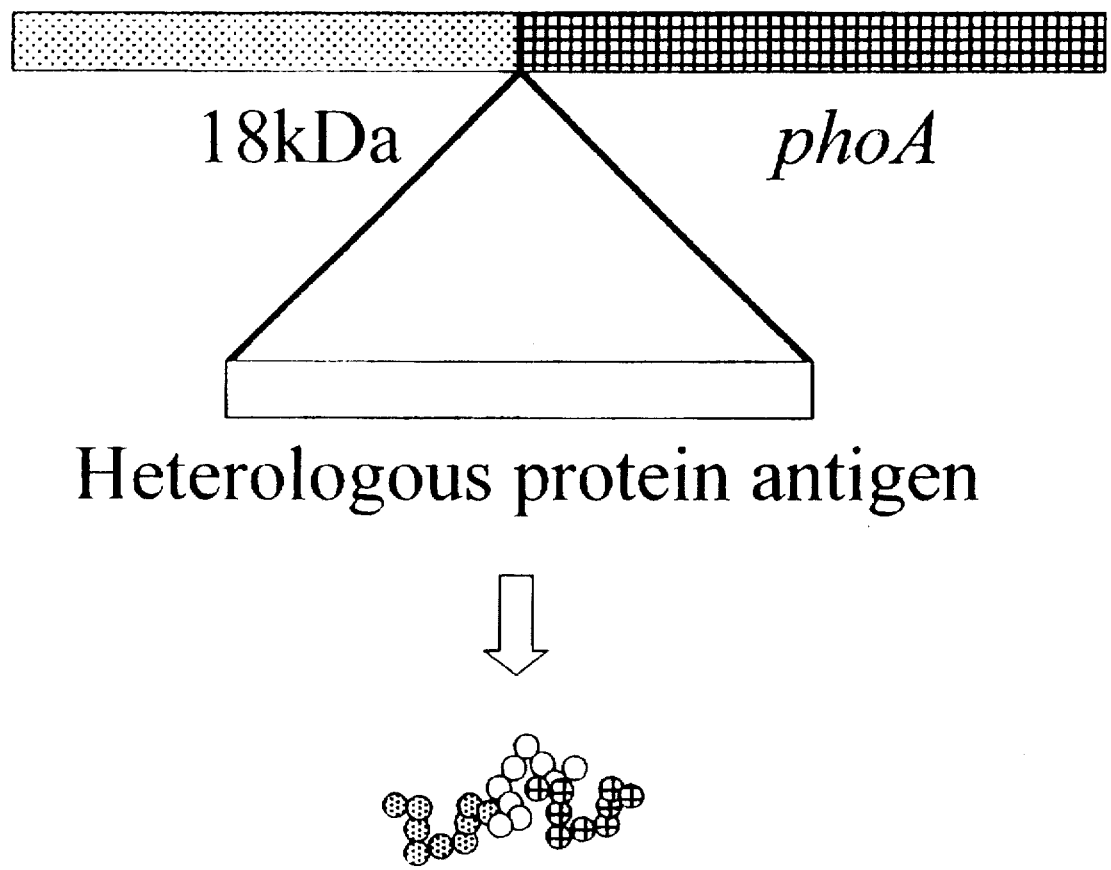
Figure 2:
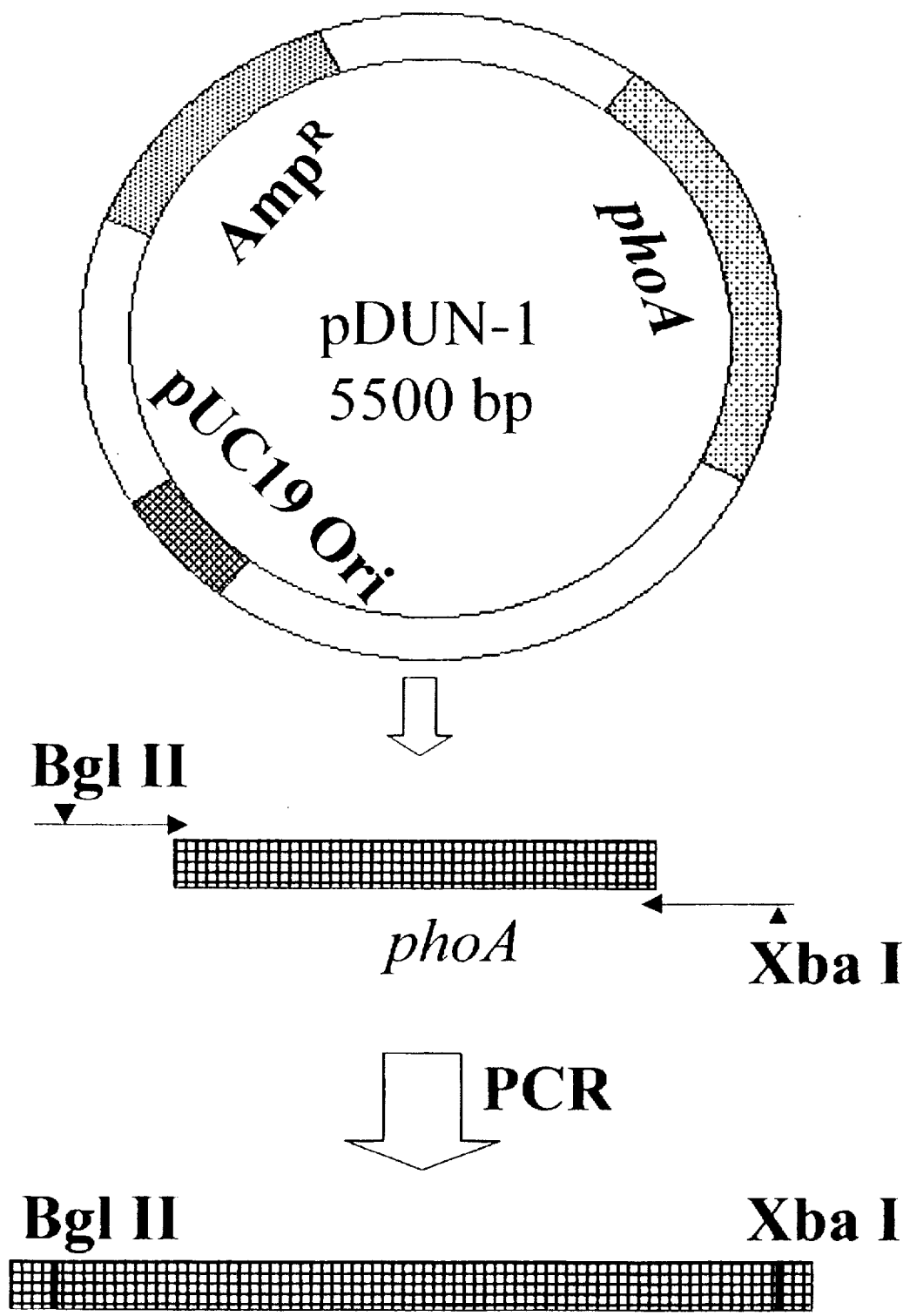

As used herein, the term "selection" shall refer to the implementation of conditions that enable the discrimination of cells displaying a required phenotype, e.g., the growth of bacteria in medium containing antibiotics to select for cells containing antibiotic resistance genes.

As used herein, the term "alternative selection" shall refer to non-antibiotic selection based on phoA or other reporters which allows non-antibiotic selection of recombinant mycobacteria based on calorimetric, fluorescent or other techniques.

As used herein, the term "protective immunity" shall refer to induction of humoral and/or cell mediated immunity that leads to protection of the host from the normal pattern of disease displayed by the pathogen.

As used herein, the term "tribrid fusion proteins" shall refer to polypeptides or proteins containing *Mycobacterium leprae* 18kDa, *E. coli* phoA, and heterologous protein sequences expressed in a single polypeptide chain.

As used herein, the term "X-P" shall refer to a chromophore which allows colorometric detection of alkaline phosphatase activity.

The present invention provides a mycobacterial shuttle vector containing sequences coding for a non-myucobacterial, non *e. coli* heterologous protein sequence, e.g., dengue virus envelope protein as a tribrid fusion containing the *M. leprae* 18Kda antigen sequence and a phoA protein antigen sequence. In one embodiment, the vector is pCR7-DEN. In another embodiment, the vector is pCR7.

Any phoA gene sequence would likely be useful in the vector and methods of the present invention. A representative example of a useful phoA gene sequence is the *E. coli* phoA gene sequence. In a preferred embodiment, the shuttle vector is useful to select for recombinants using colorimetric detection The present invention also provides a method of producing protective immunity in an animal or human host in need of such treatment, comprising the step of administering to said animal or human host an effective dose of a mycobacterial host carrying the vector of the present invention. In a preferred embodiment, the recombinant mycobacteria containing the vector is given orally, although it may be administered intradermally or by other routes. Preferably, the recombinant mycobacteria containing the vector confers protective immunity against mycobacterialmediated diseases and to diseases caused by pathogens from which the heterologous protein sequences are presented in the tribrid fusion sequence in the pCR7 vector.

It is specifically contemplated that pharmaceutical compositions may be prepared using the recombinant mycobacterial vaccine of the present invention. In such a case, the pharmaceutical composition comprises the novel recombinant mycobacterial vaccine of the present invention and a pharmaceutically acceptable carrier. A person having ordinary skill in this art would readily be able to determine, without undue experimentation, the appropriate dosages and routes of administration of the recombinant mycobacterial vaccine of the present invention.

The following examples are given for the purpose of illustrating various embodiments of the invention and are not meant to limit the present invention in any fashion.

For certain flavivirus diseases, such as dengue (DEN), no vaccine currently exists. The present invention has developed mycobacteria such as *Mycobacterium bovis* BCG, as a recombinant DNA-based multivalent vaccine that can be used to provide protective immunity against mycobacterialmediated diseases, such as tuberculosis (TB) and other infectious agents, such as dengue. The selection of recombinant mycobacterial has, to date, always depended on antibiotic selection which is not suitable for commercial exploitation or licensing by regulatory agencies. Clearly, administration of a pharmaceutical agent which confers antibiotic resistance to an individual would be counterproductive and possibly dangerous.

The present invention developed a vector that incorporates an alternative selection system for recombinant mycobacterial. An object of the present invention is the exploitation of this system to develop recombinant mycobacterial expressing foreign protein sequences, such as dengue antigens as fusion proteins that induce protective immunity against mycobacterial-mediated diseases and dengue. Recombinant mycobacteria expressing dengue antigens were constructed, tested in vitro and induction of protective immunity would be predicted in a mouse model. This technology is applicable to the development of recombinant mycobacterial vaccines that induce protection against a wide range of infectious diseases. The mycobacterial vector of the present invention has great potential for these purposes BCG is an efficacious and safe vaccine against tuberculosis. An object of the present invention is to characterize a recombinant BCG (*Mycobacterium bovis* bacille Calmette-Guerin) (rBCG) which expresses dengue-4 (DEN) virus envelope (E) protein as a tribrid fusion protein. The present invention shows the contruction and development of an *E. coli*—mycobacteria shuttle vector (pCR7) which contains the insertion sequence IS900 to facilitate stable integration of the vector into the mycobacterium chromosome. Other insertion sequences may be appropriate for integration of the vector into the chromosome of different mycobacteria.

Antigens were expressed as fusion proteins with the *Mycobacterium leprae* 18 Kda antigen and *E. coli* phoA sequences. An important advantage of the system of the present invention is the ability to select for recombinants using colorimetric detection based on phoA-encoded alkaline phosphatase (AP) activity. This novel detection system represents a significant advance over conventional antibiotic selection systems which would be unacceptable for FDA licensing and commercial development.

Thus, it is an object of the present invention to genetically manipulate the mycobacterial shuttle vector (pCR7) to contain sequences coding for the dengue-4 virus E protein as a tribrid fusion containing *M. leprae* 18Kda antigen and phoA gene sequences. The surface E protein of the flavivirus is the major immunogen for protective immunity. Electroporation into *E. coli*, *M. segmatis* and *M. bovis* BCG is performed and subsequently the recombinant dengue fusion protein were characterized by immunoblotting.

It is another object of the present invention to demonstrate protective immunity following oral or intradermal immunization with recombinant *Mycobacterium bovis* bacille Calmette-Guerin-dengue vector.

Vaccines are the most cost effective medical intervention known to prevent disease. Successful immunization requires a multicomponent immune response. The vaccine must also be safe, cheap and efficacious. The live-vectored vaccine strains of *M. bovis* BCG as described by the present invention meet these objectives. Other mycobacteria may have applications as vaccines against mycobacterial-mediated diseases.

*Mycobacterium bovis* bacille Calmette-Guerin has proven to be a very safe and effective live-attenuated bacterial vaccine which prevents tuberculosis. Its success is due to both the adjuvant effects of mycobacteria and stimulation of CMI (1). In particular, a *Mycobacterium bovis* bacille Calmette-Guerin vaccine has been administered safely to over two billion people, is the most widely used vaccine in the world, can be administered at birth, immunization, can be repeated successfully, can be given as an oral vaccine, is heat-stable, persists in vivo, is inexpensive (one dose of *Mycobacterium bovis* bacille Calmette-Guerin costing $0.06) and a worldwide distribution network with experience in *Mycobacterium bovis* bacille Calmette-Guerin vaccination already exists. Thus, *Mycobacterium bovis* bacille Calmette-Guerin offers latitude for the generation of novel recombinant vaccines expressing foreign antigens. Further, from a commercial point of view, extensive safety testing has already been undertaken on *Mycobacterium bovis* bacille Calmette-Guerin accelerating acceptability of rBCG vaccines in the marketplace.

Shuttle plasmids have been constructed for transfer and propagation of recombinant DNA between *E. coli*, *M. smegmatis* and *Mycobacterium bovis* bacille Calmette-Guerin [2]. Since *Mycobacterium bovis* bacille Calmette-Guerin grows very slowly and requires three weeks to form a usable colony of bacteria, genetic manipulations have utilized the faster growing *M. smegmatis*, which produces colonies after three days incubation. Recombinant mycobacteria expressing foreign antigens have been described based on either plasmid, bacteriophage or insertion vectors.

A number of parameters influence the induction of immunity by rBCG, including the foreign antigen being expressed, route of inoculation and genetic background of the host [2]. Different routes of immunization have also been investigated and, significantly, the oral route has been shown to be successful at inducing immunity against foreign antigens [4].

Finally, and most important, all vectors used to propagate recombinant plasmids in *Mycobacterium bovis* bacille Calmette-Guerin have utilized an encoded Tn903 (a kanamycin-resistance gene carrying transposon) and this antibiotic has been used as the selection marker for rBCG. Tn903 phenotype is selected for by the use of the antibiotic kanamycin. Clearly, rBCG incorporating Tn903 would be unacceptable to regulatory authorities. Hence, a rBCG strain which expresses dengue virus E protein without the introduction of an antibiotic resistance gene could be used to vaccinate against tuberculosis and dengue.

Methodology

Figure 3:
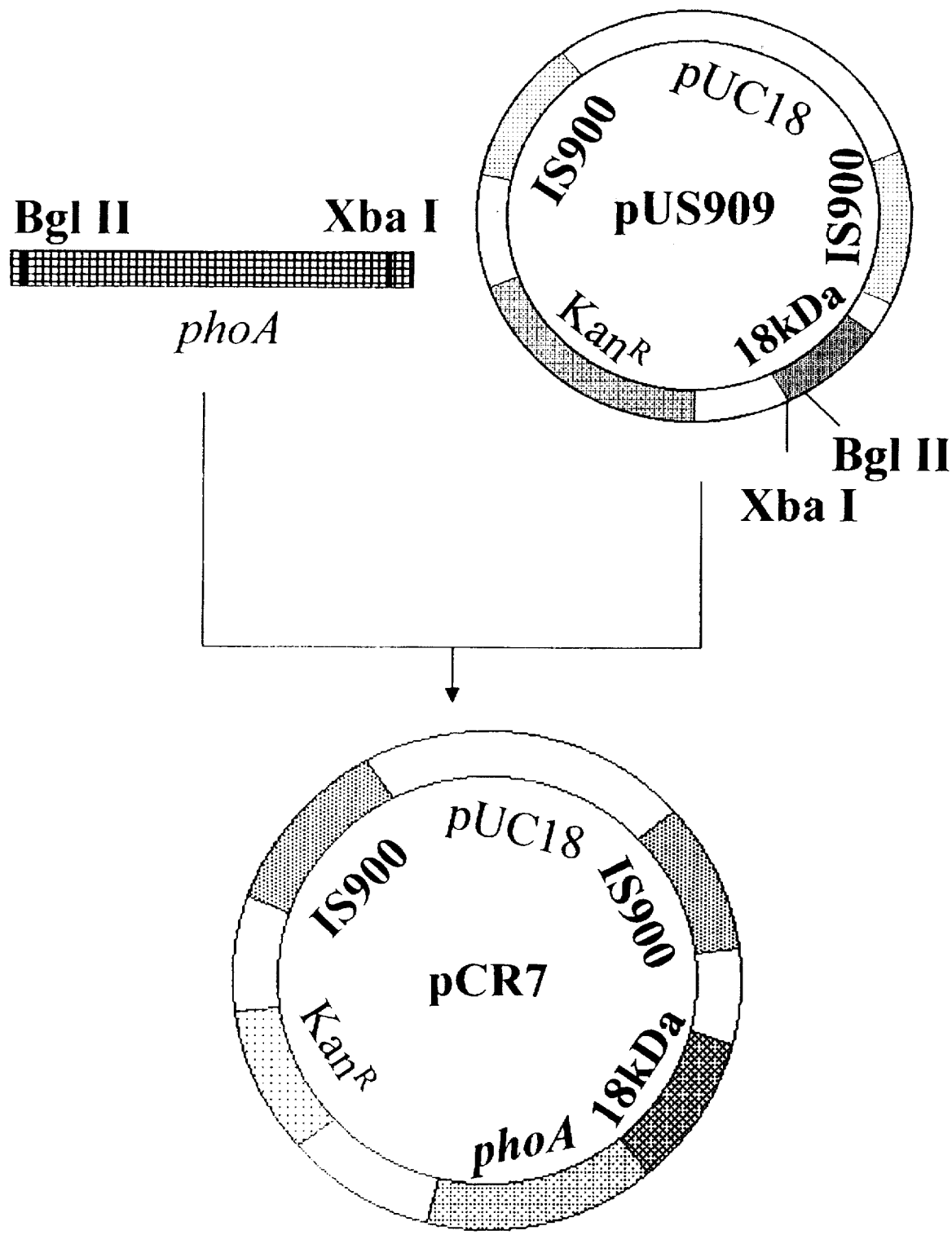

A *E. coli-mycobacterium* shuttle vector, pCR7 (FIG. 3) was constructed which, via insertion sequence 900 (IS900), integrates into the mycobacterium chromosome and permits the expression of heterologous antigens as tribrid fusion proteins. This was accomplished by placing the heterologous protein antigen sequences in frame within the mycobacterial 18 kDA gene. Selection of recombinants utilized the alkaline phosphatase activity encoded in the fusion protein and not antibiotic selection. Although the vector pCR7 contains ampicillin and kanomycin resistance genes, these were not required for identification and selection of recombinant mycobacteria. A person having ordinary skill in this art would readily recognize that one could use, therefore, a pCR7-derived vector lacking all antibiotic resistance genes for the purposes described herein.

Tribrid fusions were constructed which express the dengue-4 E protein. The dengue-4 E gene was amplified by PCR using primers that incorporate recognition sites for the restriction enzyme BglII. Additional nucleotides were included in the primers to maintain the proper reading frame.

Figure 4:
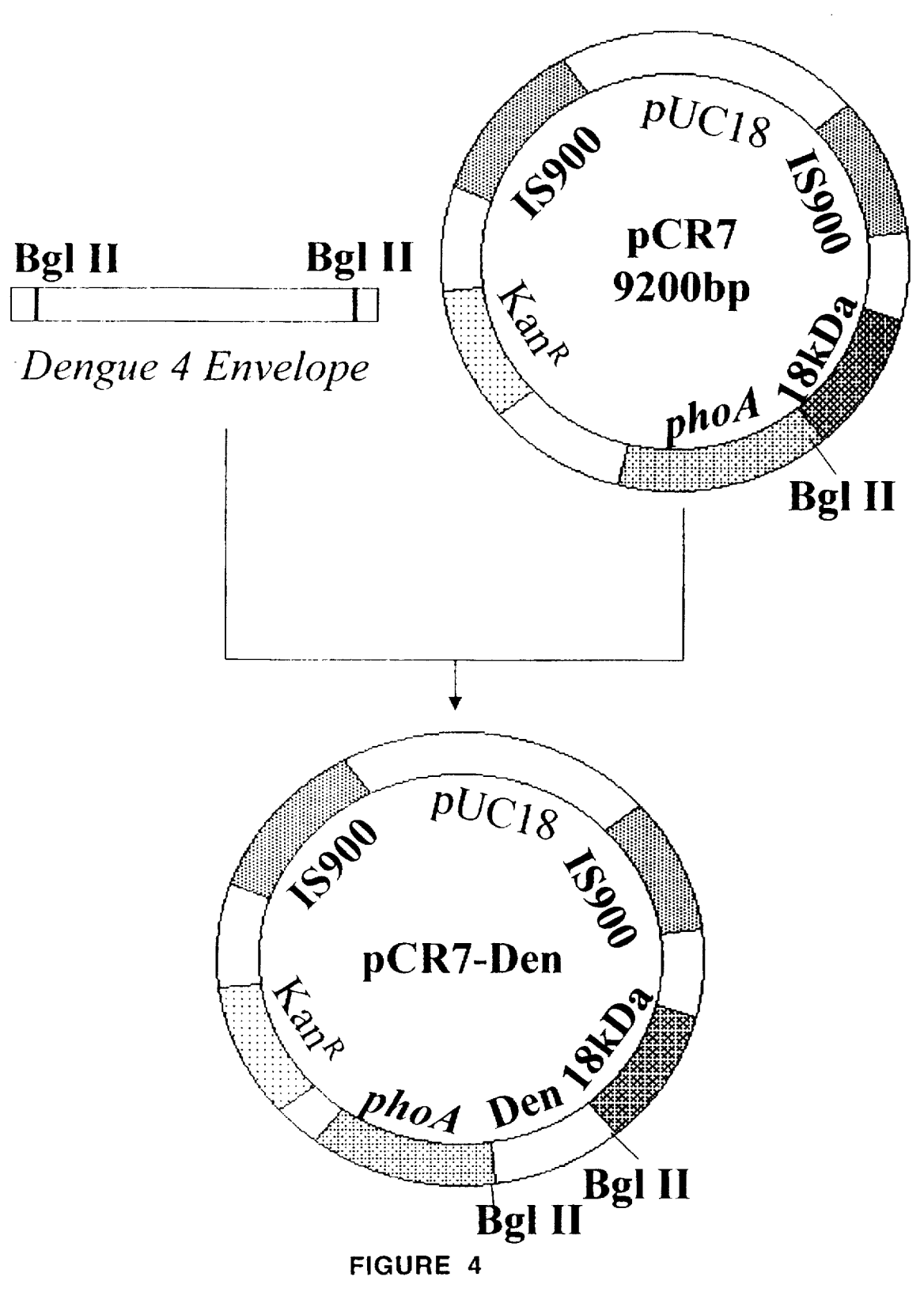

The amplified cDNA was ligated into the BglII site of pCR7 (shown in FIG. 4) and propagated in *E. coli* CC118 (phoA) [5]. Transformants were screened for an alkaline phosphase activity by observing a blue phenotype on L-X-P agar and confirmation by restriction digestion. Putative recombinants (pCR7-DEN) were confirmed for proper orientation and retention of a continuous reading frame. The dengue-tribrid fusion proteins were characterized using established techniques, including alkaline phosphatase activity and immunoblotting.

Following electroporation, the expression of pCR7-DEN in *M. smegmatis* and *Mycobacterium bovis* bacille Calmette-Guerin (Pasteur strain) was also determined. The recovery of blue colonies identified the recombination of the fusion construction into the mycobacterial chromosome which was confirmed by Southern analysis of restricted chromosomal preparations.

Expression of the pCR7-DEN fusion proteins was investigated by methods outlined above. Variation in the level of expression of fusion proteins and stability of the constructs within the chromosome (following sequential passage and storage) was investigated. The plasmid was stably inserted in the mycobacterial chromosome and the colonies maintained, alkaline phosphatase activity (and a blue color) was examined following passage.

Expression of a 18 Kda: PhoA fusion protein in mycobacterium

The present invention describes a plasmid vector (pCR7) which expresses the *M. leprae* 18kDa antigen fused to *E. coli* PhoA. The plasmid also contains IS900 elements which allow integration into the mycobacterium chromosome. *M. smegmatis* transformed with pCR7 showed alkaline phosphatase (AP) activity on X-P containing agar. The predicted 61 kDa fusion protein was observed by immunoblotting using both a monoclonal antibody to alkaline phosphatase and to the 18kDa protein.

Transformants with a single copy of the construct vary in the level of alkaline phosphatase activity and have been passed stably without antibiotic pressure. Low level expression from the 18kDa promoter is observed following in vitro growth. However, recovery of *M. smegmatis* harboring pCR7 from mouse J774 macrophage cells showed significant up regulation of the o 18kDa::PhoA fusion protein. Thus, pCR7 has characteristics which may allow non-antibiotic selection of stable recombinant strains and showed enhanced expression of the encoded fusion protein in macrophages and/or other antigen presenting cells.

Figure 5:
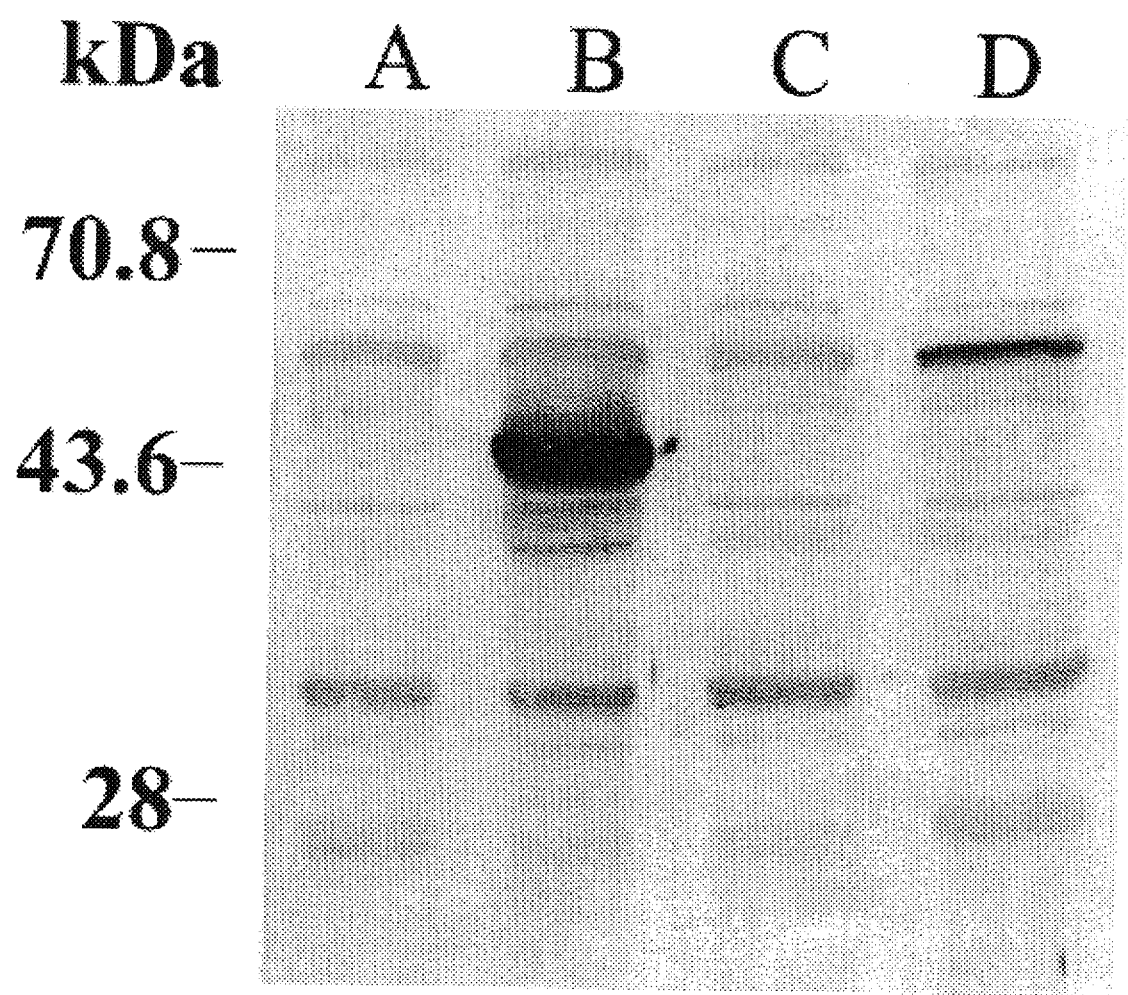
Figure 6:
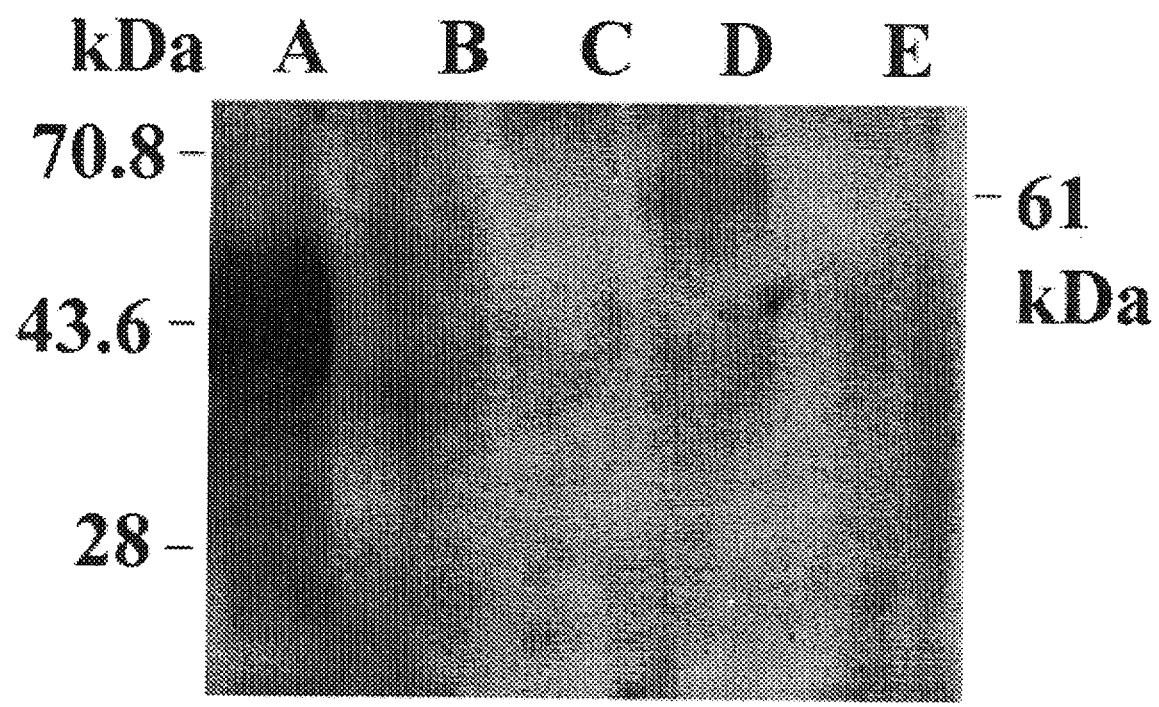
Figure 7:
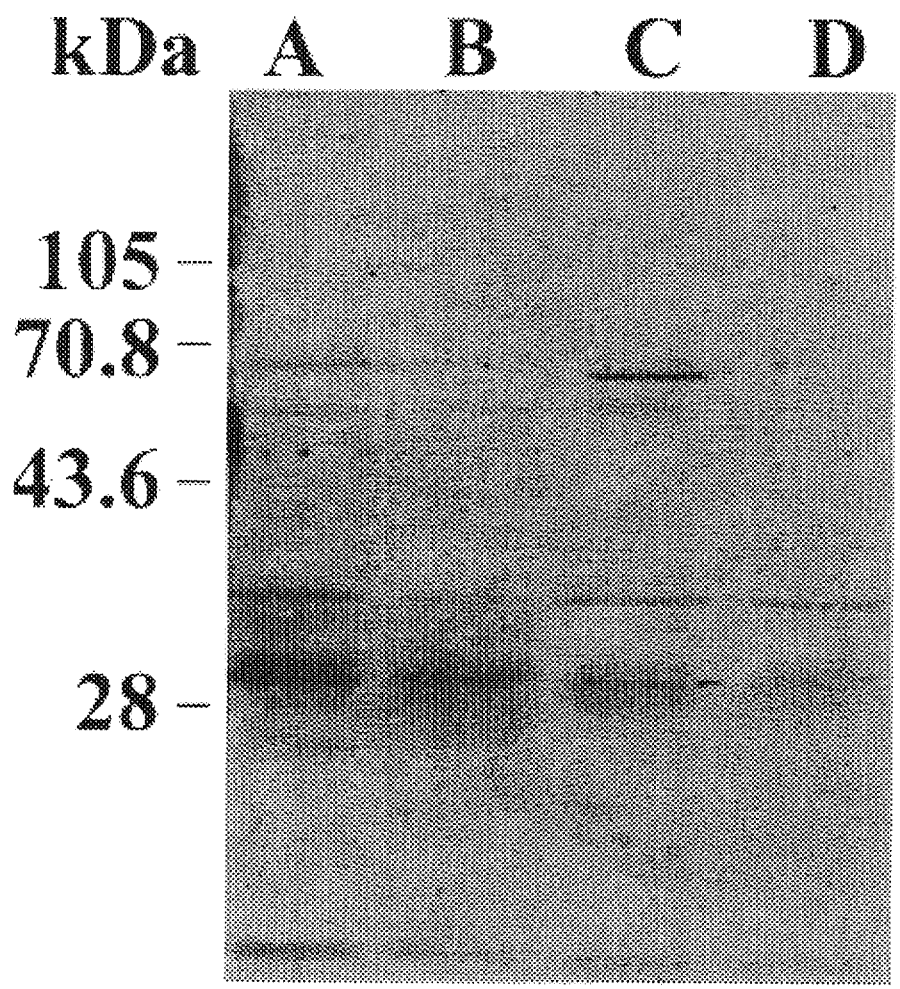

The expression of the pCR7 18kDa::phoA fusion protein was evaluated in recombinant *E. coli* carrying the vector. As shown in FIG. 5, whole cell lysates of *E. coli* harboring pCR7 but not pUS909 showed an immunoreactive band at 61 kDa using an antibody to PhoA. Further, as shown in FIG. 6, the anti-phoA reactive fusion protein was observed at the same molecular weight in lysates of *M. smegmatis* harboring this vector. The same reactive band representing the fusion protein was observed using a monoclonal antibody (L5) directed to the *M. leprae* 18kDa protein (FIG. 7).

Figure 8:
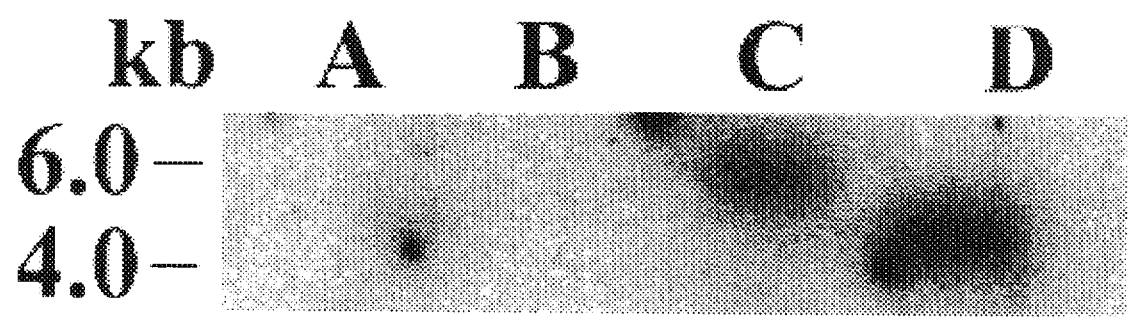
Figure 9:
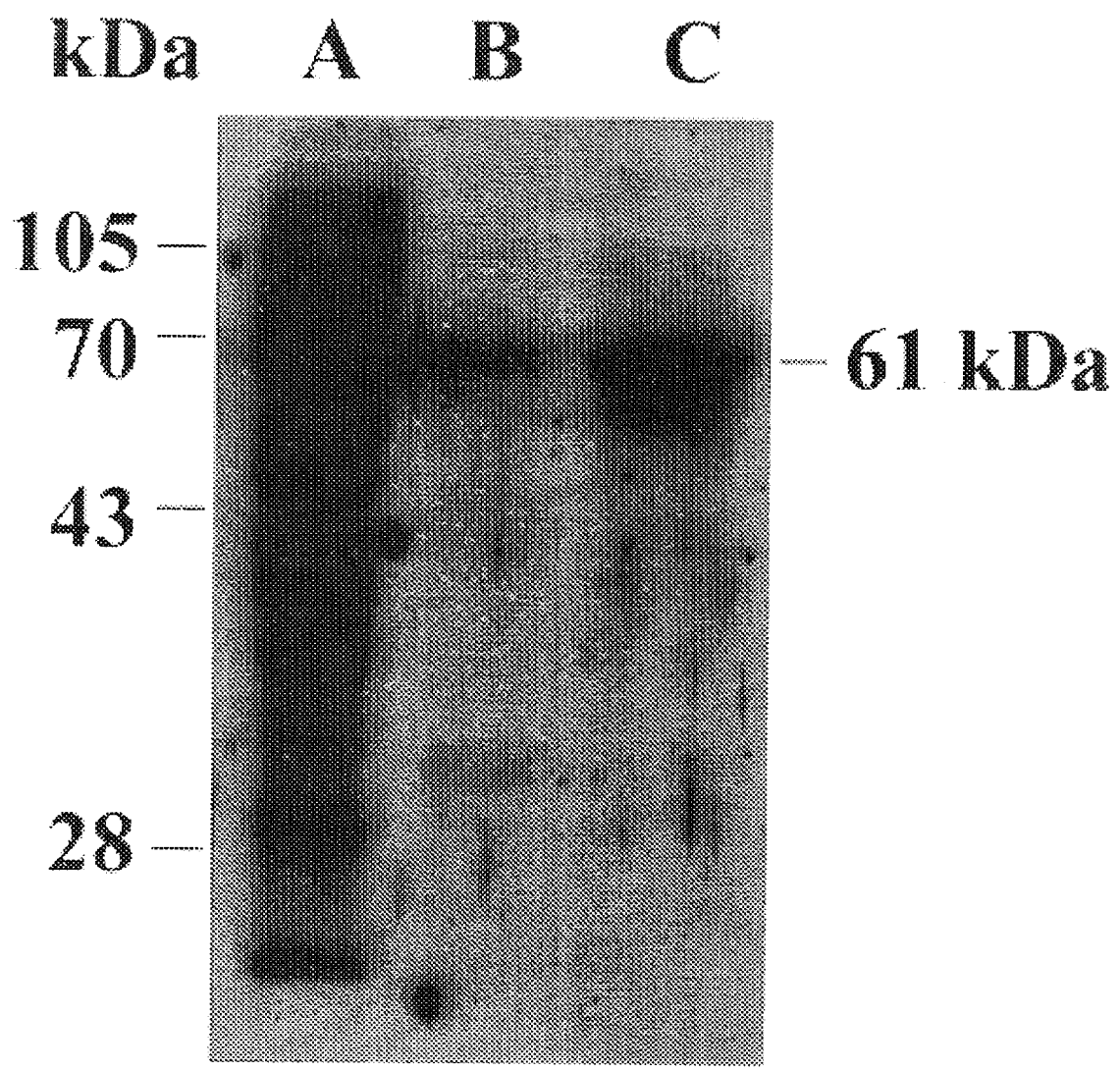
Figure 10:
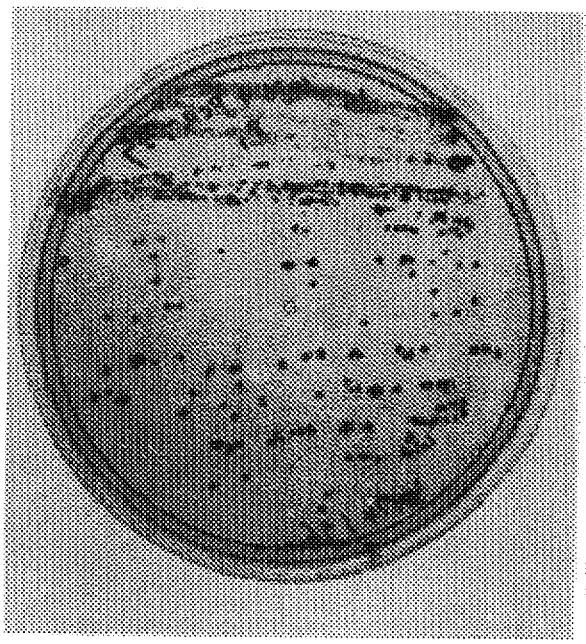
Figure 10:
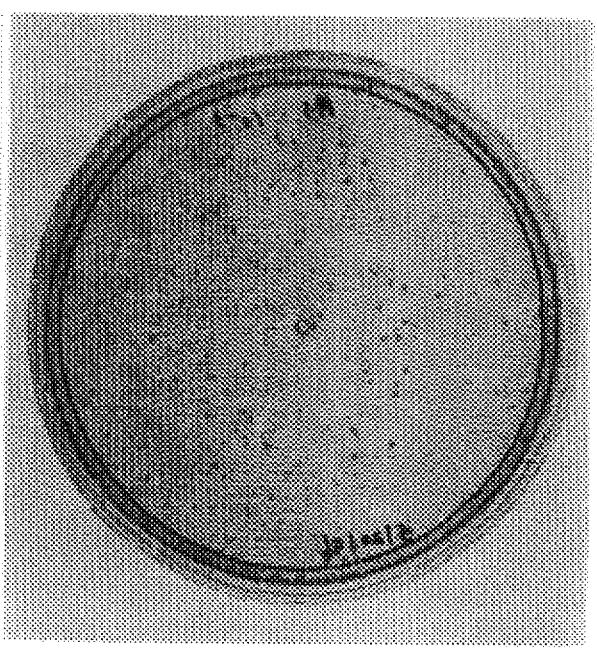

FIG. 8 demonstrates integration of one copy of pCR7 into the chromosome of *M. smegmatis*. FIG. 9 shows that the expression of the fusion protein is upregulated in the J774 macrophage cell line. In FIG. 10, the blue phenotype of the recombinant mycobacteria harboring the pCR7 and expressing the fusion protein on agar containing the alkaline phosphatase substrate X-P is shown.

The following references were cited herein:

1. Brown (1983). In the *Biology of the Mycobacteria,* Volume 2, pp 173–234.

2. Dale et al. (1993). Multivalent BCG vaccines. In, *Novel delivery systems for oral vaccines.* pp 87–110.

3. Fomukong et al. (1992). *J. App. Bact.* 72, 126–133.
4. Langermann et al. (1994). *Nature* 372, 552–555.
5. Phillips et al. (1992). *J. Micro. Meth.* 16, 13–22.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A *Mycobacterium-E. coli* shuttle vector containing a non-mycobacterial, non-*e. coli* heterologous protein antigen sequence as a tribrid fusion with the *M. leprai* 18kDa antigen sequence and a phoA protein antigen sequence.

2. The shuttle vector of claim 1, wherein said vector is pCR7.

3. The shuttle vector of claim 1, wherein said phoA sequence is a *E. coli* phoA.

4. The shuttle vector of claim 1, wherein said heterologous protein antigen is dengue virus-4 E protein.

5. The shuttle vector of claim 1, wherein said vector is useful to select for recombinant mycobacteria using calorimetric detection.

6. The shuttle vector of claim 1, wherein said vector is useful to select for recombinant mycobacteria using an alkaline phosphatase based detection technique.

* * * * *